US00PP23940P2

(12) United States Plant Patent
Bergman

(10) Patent No.: US PP23,940 P2
(45) Date of Patent: Oct. 1, 2013

(54) ***HIBISCUS* PLANT NAMED 'TOBAGO WIND'**

(50) Latin Name: *Hibiscus rosa-sinensis*
Varietal Denomination: Tobago Wind

(75) Inventor: Wendy R. Bergman, Hollister, CA (US)

(73) Assignee: Aris Horticulture Inc., Barberton, OH (US)

( * ) Notice: Subject to any disclaimer, the term of this patent is extended or adjusted under 35 U.S.C. 154(b) by 67 days.

(21) Appl. No.: 13/373,921

(22) Filed: Dec. 5, 2011

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — C. A. Whealy

(57) ABSTRACT

A new and distinct cultivar of *Hibiscus* plant named 'Tobago Wind', characterized by its upright, uniformly mounded and dense plant habit appropriate for container production; glossy dark green-colored leaves; uniform, freely and early flowering habit; white-colored flowers with red purple-colored centers; and good postproduction and garden performance.

2 Drawing Sheets

Botanical designation: *Hibiscus rosa-sinensis.*
Cultivar denomination: 'TOBAGO WIND'.

BACKGROUND OF THE INVENTION

The present invention relates to a new and distinct *Hibiscus* plant, botanically known as *Hibiscus rosa-sinensis* and hereinafter referred to by the name 'Tobago Wind'.

The new *Hibiscus* plant is a product of a planned breeding program conducted by the Inventor in Alva, Fla. The objective of the breeding program is to create new freely-branching *Hibiscus* plants with a dense, uniform and compact plant habit appropriate for container production, early and uniform flowering habit, numerous flowers per lateral branch, desirable flower color and good garden performance.

The new *Hibiscus* plant originated from a cross-pollination made by the Inventor in Alva, Fla. in October, 2004 of a proprietary selection of *Hibiscus rosa-sinensis* identified as code number YB-2256, not patented, as the female, or seed, parent with a proprietary selection of *Hibiscus rosa-sinensis* identified as code number YB-2195, not patented, as the male, or pollen, parent. The new *Hibiscus* plant was discovered and selected by the Inventor as a single flowering plant within the progeny of the stated cross-pollination in a controlled greenhouse environment in Alva, Fla. on Aug. 23, 2005.

Asexual reproduction of the new *Hibiscus* plant by vegetative terminal cuttings in a controlled greenhouse environment in Alva, Fla. since January, 2006 has shown that the unique features of this new *Hibiscus* plant are stable and reproduced true to type in successive generations.

SUMMARY OF THE INVENTION

Plants of the new *Hibiscus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tobago Wind'.

These characteristics in combination distinguish 'Tobago Wind' as a new and distinct *Hibiscus* plant:

1. Upright, uniformly mounded and dense plant habit appropriate for container production.
2. Glossy dark green-colored leaves.
3. Uniform, freely and early flowering habit.
4. White-colored flowers with red purple-colored centers.
5. Good postproduction and garden performance.

Plants of the new *Hibiscus* can be compared to plants of the female parent selection. Plants of the new *Hibiscus* differ from plants of the female parent selection in the following characteristics:

1. Plants of the new *Hibiscus* are more compact than plants of the female parent selection.
2. Plants of the new *Hibiscus* are more freely branching than plants of the female parent selection.
3. Plants of the new *Hibiscus* have larger flowers than plants of the female parent selection.
4. Flowers of plants of the new *Hibiscus* are whiter in color than flowers of plants of the female parent selection.

Plants of the new *Hibiscus* can be compared to plants of the male parent selection. Plants of the new *Hibiscus* differ from plants of the male parent selection primarily in flower color as plants of the male parent selection have light pink-colored flowers. In addition, plants of the new *Hibiscus* have larger flowers than plants of the male parent selection.

Plants of the new *Hibiscus* can be compared to plants of the *Hibiscus rosa-sinensis* 'Cool Wind', disclosed in U.S. Plant Pat. No. 12,887. In side-by-side comparisons conducted in Alva, Fla., plants of the new *Hibiscus* differed from plants of 'Cool Wind' in the following characteristics:

1. Plants of the new *Hibiscus* were more vigorous than plants of 'Cool Wind'.
2. Plants of the new *Hibiscus* flowered later than plants of 'Cool Wind'.
3. Plants of the new *Hibiscus* had larger flowers than plants of 'Cool Wind'.
4. Plants of the new *Hibiscus* are more low temperature tolerant than plants of 'Cool Wind'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Tobago Wind' grown in a container.

The photograph on the second sheet comprises a close-up view of a typical flowering plant of 'Tobago Wind'.

DETAILED BOTANICAL DESCRIPTION

The aforementioned photographs and following observations, measurements and values describe plants grown during the summer in 15-cm containers in a fiberglass-covered greenhouse in Alva, Fla. and under environmental conditions and cultural practices which closely approximate commercial *Hibiscus* production. During the production of the plants, day temperatures ranged from 20° C. to 38° C., night temperatures ranged from 15° C. to 24° C. and light levels ranged from 3,000 to 4,000 foot-candles. Plants were pinched two times and were 27 weeks old when the photographs and the description were taken. In the description, color references are made to The Royal Horticultural Society Colour Chart, 2007 Edition, except where general terms of ordinary dictionary significance are used.

Botanical classification: *Hibiscus rosa-sinensis* 'Tobago Wind'.

Parentage:

*Female, or seed, parent*.—Proprietary selection of *Hibiscus rosa-sinensis* identified as code number YB-2256.

*Male or pollen parent*.—Proprietary selection of *Hibiscus rosa-sinensis* identified as code number YB-2195.

Propagation:

*Type*.—By vegetative terminal cuttings.

*Time to initiate roots*.—About 10 days at temperatures of 24° C.

*Time to develop roots*.—About four weeks at temperatures of 24° C.

*Root description*.—Thick, fibrous; white in color.

*Rooting habit*.—Moderate branching; moderately dense.

Plant description:

*Plant form and growth habit*.—Perennial, evergreen, upright, compact, uniformly mounded and dense; moderately vigorous growth habit.

*Branching habit*.—Freely branching habit with lateral branches potentially develop at every node; pinching enhances lateral branch development.

*Plant height*.—About 40 cm.

*Plant diameter* (*area of spread*).—About 34 cm.

Lateral branch description:

*Length*.—About 24 cm.

*Diameter*.—About 7 mm.

*Internode length*.—About 1.8 cm.

*Aspect*.—Upright to slightly outwardly spreading.

*Texture*.—Immature, smooth; mature, woody and rough.

*Color, immature*.—Close to 146A.

*Color, mature*.—Close to 197A.

Foliage description:

*Arrangement*.—Alternate, single; numerous; symmetrical.

*Length*.—About 7 cm.

*Width*.—About 5.9 cm.

*Shape*.—Ovate with cordate tendencies.

*Apex*.—Acute to acuminate.

*Base*.—Obtuse to cordate.

*Margin*.—Serrate.

*Texture, upper and lower surfaces*.—Smooth, glabrous.

*Luster, upper surface*.—Glossy.

*Luster, lower surface*.—Somewhat glossy.

*Venation pattern*.—Pinnate; arcuate.

*Color*.—Developing leaves, upper surface: More green than N137A. Developing leaves, lower surface: Close to 137B. Fully expanded leaves, upper surface: Darker green than 147A; venation, close to 147A. Fully expanded leaves, lower surface: Close to 137A to 137B; venation, close to 146B.

*Petiole*.—Length: About 3 cm. Diameter: About 3.5 mm. Texture, upper and lower surfaces: Smooth, glabrous. Color, upper and lower surfaces: Between 137A and 146A.

Flower description:

*Flower arrangement and flowering habit*.—Rounded star-shaped flowers arranged at terminal leaf axils; uniform and freely flowering habit with about two to three flowers per terminal; flowers face mostly upright to outwardly.

*Natural flowering season*.—Plants of the new *Hibiscus* flower naturally during the spring and summer or during periods of warm weather; plants flower year-round in the greenhouse.

*Flower longevity*.—Flowers last about two to three days on the plant; flowers persistent.

*Flower diameter*.—About 12 cm.

*Flower length* (*height*).—About 7.25 cm.

*Flower bud*.—Resistance to abscission during shipping: Plants of the new *Hibiscus* have been observed to resist flower bud drop when stored in a closed box for five days at 13° C. Length: About 3.2 cm. Diameter: About 1.2 cm. Shape: Ovoid. Color: Close to 137A.

*Petals*.—Arrangement: Corolla consists of five petals that are fused at base; petals imbricate. Length: About 7.25 cm. Width: About 5.25 cm. Shape: Roughly spatulate. Apex: Rounded. Base: Attenuate. Margin: Entire; slightly undulate. Texture: Smooth, glabrous; satiny; veins prominent on the lower surface. Color: When opening, upper surface: Close to 155A to 155D; towards the base, close to N57A. When opening, lower surface: Close to 155A. Fully opened, upper surface: Close to 155A to 155D; towards the apex, close to 158A; towards the base, close to N57A; color does not change with development. Fully opened, lower surface: Close to 155A; towards the apex, close to 158A; color does not change with development.

*Sepals*.—Appearance: Five to six sepals fused into a tubular star-shaped calyx. Length: About 3.2 cm. Width: About 1 cm. Shape: Lanceolate. Apex: Sharply acute. Margin: Entire. Texture, upper surface: Smooth, glabrous; waxy. Texture, lower surface: Slightly pubescent. Color, upper surface: Close to 144A. Color, lower surface: More green than 137A.

*Bracts*.—Appearance: About seven to eight fused at base. Length: About 1.6 cm. Width: About 4 mm. Shape: Lanceolate. Apex: Acute. Margin: Entire. Texture, upper surface: Smooth, glabrous. Texture, lower surface: Sparsely pubescent. Color, upper and lower surfaces: Close to 137A.

*Peduncles*.—Length: About 4.75 cm. Diameter: About 2 mm. Aspect: Upright. Strength: Strong, flexible. Texture: Smooth, glabrous. Color: Close to 144A.

*Reproductive organs*.—Androecium: Stamen number: Numerous, about 50 per flower. Filament length: About 3.5 mm. Filament color: Close to 155A. Anther shape: Oblong. Anther length: About 1 mm. Anther color: Close to 13A. Amount of pollen: Scarce. Pollen color: Close to 13A. Gynoecium: Pistil number: One per flower. Pistil length: About 6.9 cm. Style length: About 5.7 cm. Style texture: Smooth, glabrous; waxy. Style color: Close to 158A; towards the base, close to 53C. Stigma appearance: Five-parted, rounded. Stigma color: Close to 9A. Ovary color: Close to 11D.

*Seeds and fruits*.—Seed and fruit production has not been observed on plants of the new *Hibiscus*.

Garden performance: Plants of the new *Hibiscus* have been observed to have good garden performance and to tolerate wind, rain and temperatures ranging from about 1° C. to about 38° C.

Pathogen & pest resistance: Plants of the new *Hibiscus* grown under Florida production conditions have not been shown to be susceptible to pathogens common to *Hibiscus* such as *Pseudomonas, Pythium* and *Phytophthora*. Plants of the new *Hibiscus* have not been observed to be resistant to pests and other pathogens.

It is claimed:

1. A new and distinct *Hibiscus* plant named 'Tobago Wind' as illustrated and described.

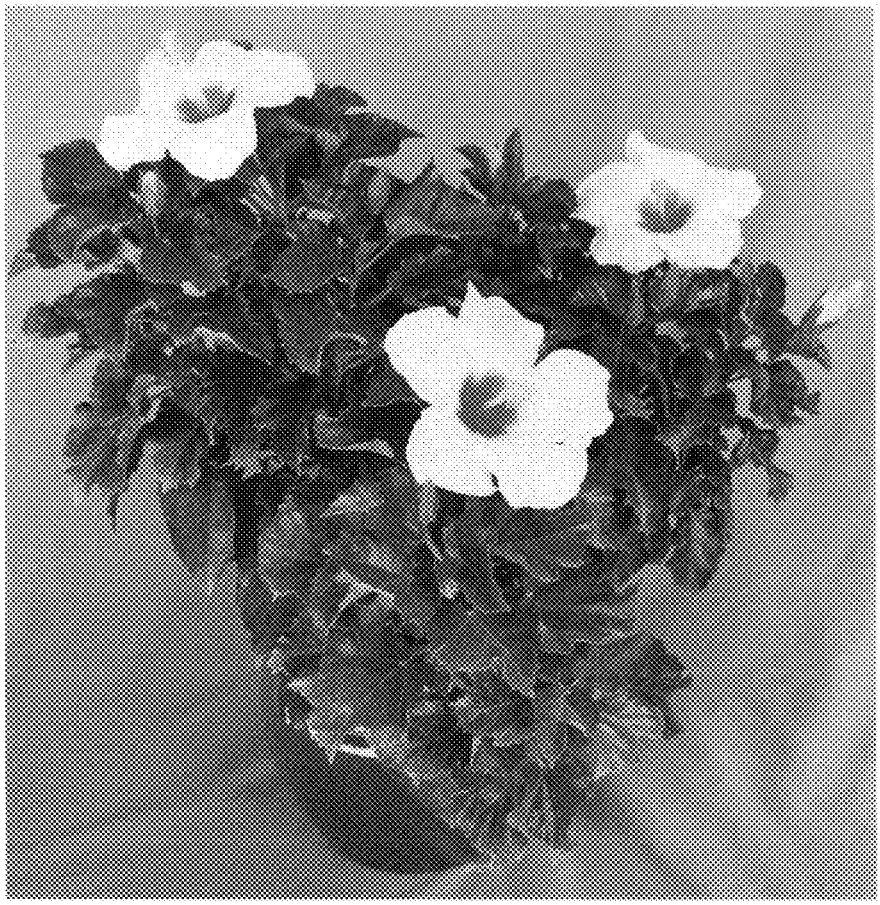

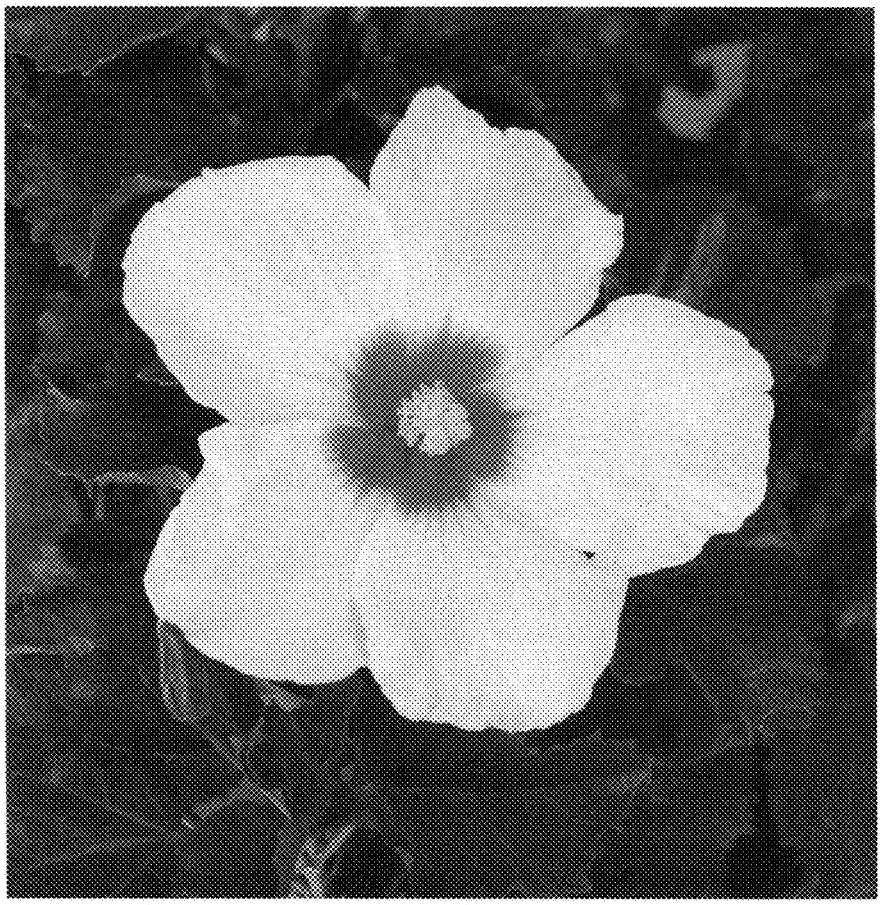

* * * * *